US010548787B2

(12) United States Patent
Habashi et al.

(10) Patent No.: US 10,548,787 B2
(45) Date of Patent: Feb. 4, 2020

(54) BODY POSITIONING MATTRESS

(71) Applicant: SLH Holdings LLC, Baltimore, MD (US)

(72) Inventors: Nader M. Habashi, Annapolis, MD (US); Patricia L. Andrews, Arnold, MD (US)

(73) Assignee: SLH Holdings LLC, Baltimore, MD (US)

( * ) Notice: Subject to any disclaimer, the term of this patent is extended or adjusted under 35 U.S.C. 154(b) by 561 days.

(21) Appl. No.: 14/658,856

(22) Filed: Mar. 16, 2015

(65) Prior Publication Data

US 2015/0190294 A1 Jul. 9, 2015

Related U.S. Application Data

(63) Continuation of application No. 11/004,776, filed on Dec. 3, 2004, now abandoned.

(60) Provisional application No. 60/526,727, filed on Dec. 3, 2003.

(51) Int. Cl.
*A61G 7/057* (2006.01)
*A61G 7/005* (2006.01)
*A61F 5/37* (2006.01)

(52) U.S. Cl.
CPC ............ *A61G 7/057* (2013.01); *A61F 5/3776* (2013.01); *A61G 7/005* (2013.01); *A61G 7/05753* (2013.01)

(58) Field of Classification Search
CPC .... A61G 7/057; A61G 7/005; A61G 7/05753; A61G 13/04; A61G 13/1275; A47C 19/045; A61F 5/3776

USPC ........ 5/709, 601, 610, 702, 655.4, 911, 913
See application file for complete search history.

(56) References Cited

U.S. PATENT DOCUMENTS

| 1,925,425 | A | | 9/1933 | Wilent |
| 2,508,449 | A | | 5/1950 | Davis |
| 2,787,506 | A | | 4/1957 | Travisano |
| 2,887,691 | A | | 5/1959 | Talarico et al. |
| 3,089,692 | A | | 5/1963 | Blomqvist |
| 3,293,667 | A | * | 12/1966 | Ohrberg ................. A61G 7/005 |
| | | | | 5/610 |
| 3,423,773 | A | | 1/1969 | Yamate |
| 3,568,669 | A | | 3/1971 | Stites |
| 3,609,777 | A | | 10/1971 | Agnew et al. |
| 3,640,520 | A | | 2/1972 | Wieland et al. |
| 3,745,998 | A | | 7/1973 | Rose |
| 3,783,863 | A | | 1/1974 | Kliever |
| 3,997,926 | A | | 12/1976 | England |
| 4,015,836 | A | | 4/1977 | Redington et al. |
| 4,045,078 | A | | 8/1977 | Shine |
| 4,175,550 | A | | 11/1979 | Leininger et al. |
| 4,356,577 | A | | 11/1982 | Taylor et al. |
| 4,613,997 | A | | 9/1986 | Langdale |
| 4,672,697 | A | | 6/1987 | Schürch |

(Continued)

*Primary Examiner* — Nicholas F Polito
(74) *Attorney, Agent, or Firm* — Corinne Marie Pouliquen

(57) ABSTRACT

A body positioning mattress and a method of positioning a patient or person 0 to 90 degrees or greater in an upright supine or prone position while maintaining neutral skeletal alignment (non-flexed position) wherein a vacuum process can be applied to the body positioning mattress to remove air thereby molding the mattress around the body of the patient or person to maintain position. Further, the mattress may be placed onto a manual or motorized bed frame to position and maintain a patient or person 0 to 90 degrees or greater in the supine or prone position.

6 Claims, 5 Drawing Sheets

(56) References Cited

U.S. PATENT DOCUMENTS

| | | |
|---|---|---|
| 4,688,283 A | 8/1987 | Jacobson et al. |
| 4,787,104 A | 11/1988 | Grantham |
| 4,944,060 A | 7/1990 | Peery et al. |
| 4,982,465 A | 1/1991 | Nagata et al. |
| 4,987,622 A | 1/1991 | Shockey |
| 5,003,654 A | 4/1991 | Vrzalik |
| 5,072,463 A | 12/1991 | Willis |
| 5,168,588 A | 12/1992 | Chan |
| 5,345,632 A | 9/1994 | Langenaeken et al. |
| 5,416,936 A | 5/1995 | Chan |
| 5,418,990 A | 5/1995 | Risasen |
| 5,487,196 A | 1/1996 | Wilkinson et al. |
| 5,720,061 A | 2/1998 | Giori et al. |
| 5,745,941 A | 5/1998 | Miller, Sr. |
| 5,790,996 A | 8/1998 | Narfström |
| 5,826,286 A | 10/1998 | Cranston |
| 5,836,027 A | 11/1998 | Leventhal et al. |
| 5,966,762 A | 10/1999 | Wu |
| 5,983,424 A | 11/1999 | Naslund |
| 6,016,582 A | 1/2000 | Larson |
| 6,038,722 A | 3/2000 | Giori et al. |
| 6,053,880 A | 4/2000 | Sleichter, III |
| 6,058,533 A | 5/2000 | Nelson |
| 6,070,281 A | 6/2000 | Reich |
| 6,073,290 A | 6/2000 | Miller, Sr. |
| 6,243,897 B1 | 6/2001 | Sumiya |
| 6,260,222 B1 | 7/2001 | Lin |
| 6,353,949 B1 | 3/2002 | Falbo |
| 6,484,332 B2 | 11/2002 | Korver, II et al. |
| 6,598,250 B1 | 7/2003 | Pekar |
| 6,637,055 B1 | 10/2003 | Nanan |
| 6,775,867 B1 | 8/2004 | Kuphal |
| 6,817,363 B2 * | 11/2004 | Biondo ................. A61G 5/006 128/845 |
| 6,829,797 B2 | 12/2004 | Partian |
| 6,862,762 B1 | 3/2005 | Johnson |
| 7,327,863 B1 | 2/2008 | Green et al. |
| 8,240,310 B2 * | 8/2012 | Soung ................. A61B 6/0428 128/845 |
| 8,387,789 B2 * | 3/2013 | Baker ................. B63B 35/7946 206/315.1 |
| 9,549,865 B2 * | 1/2017 | Hiebert ................. A61F 5/05833 |
| 2002/0148045 A1 | 10/2002 | Giori et al. |
| 2004/0003471 A1 | 1/2004 | VanSteenburg |
| 2005/0120479 A1 * | 6/2005 | Habashi ................. A61G 7/005 5/610 |
| 2006/0000021 A1 * | 1/2006 | Hayes ................. A47C 20/08 5/618 |
| 2015/0190294 A1 * | 7/2015 | Habashi ................. A61G 7/005 5/610 |

* cited by examiner

BODY POSITIONING MATTRESS

CROSS-REFERENCE TO RELATED APPLICATIONS

This application is a continuation of U.S. patent application Ser. No. 11/004,776 filed Dec. 3, 2004, which claims priority to U.S. Provisional Patent Application No. 60/526,727 filed Dec. 3, 2003.

FIELD OF THE INVENTION

The invention relates to the field of body positioning mattresses for humans. More particularly, the present invention relates to a mattress and method of providing contour support while allowing a body to be positioned from 0° to 90° or greater in an upright position, either supine or prone, while continuing to provide contour support. This method may be essential to patients confined to a supine position, or immobile while in the Intensive Care Unit (ICU).

BACKGROUND OF THE INVENTION

It can be appreciated that a mattress has been used for years. Typically, a mattress is used to support a human body for rest or during an illness where a person is bedridden.

While these mattresses are suitable for comfort and to support a person during their phase of bed rest, it does not provide support during an upright position of up to 90° or greater. A person would lose contour support if a conventional mattress was used in an upright position of up to 90° or greater, whether in the supine or prone position.

SUMMARY OF THE INVENTION

The present invention relates to a body positioning mattress that allows a body to descend into the mattress, which conforms to the shape of the body, preventing slippage. Utilizing a vacuum system to remove air, the body descends deeper into the mattress of the present invention, conforming to the shape of the body. The increased density of the mattress caused by the vacuum process, will create support and mold a form around the body. Additional layers may be utilized to provide additional support and padding, promoting comfort and adding measures to prevent skin breakdown.

When patients are confined to a supine position in the ICU, significant deterioration of pulmonary function may occur. Immobility issues that may compromise pulmonary function stem from, but are not limited to: hemodynamic instability, refractory intracranial hypertension and/or increased abdominal pressures. In instances of immobility, patients may benefit from the ability to be positioned upright up to 90° in a supine or prone position while remaining on a bed. For example, many medical therapeutic treatments require alteration in body position such as head position for the reduction of risk of aspiration and head elevation for the reduction of intracranial pressure. The supine position maximizes the compressive effect of the heart, lungs and chest wall. Compression of lung tissue leads to additional airway closure and alveolar collapse. The heart and mediastinal structures impose additional hydrostatic pressure on dependent lung regions. The weight of a blood filled heart compresses the broad middle and dependent lung regions toward the thorax and the spine. By placing the patient in an upright 'standing' position rather than an upright 'sitting' position, the abdominal contents are no longer directed cephalad (towards the head) which encroaches on the thoracic cavity, minimizing lung expansion. By improving ventilation to the dependent lung regions, patients may be weaned from a ventilator faster, thereby decreasing risks of ventilator associated pneumonia and reducing hospital stays, which may reduce hospital costs.

Support of the human body with a positioning mattress according to the present invention may be accomplished by creating an adaptive shape for the body. The mattress is preferably encased within a cover which may utilize a vacuum process to remove air from within the mattress cover. By placing the human body on the mattress and then applying the vacuum process, the body will sink into the mattress as the mattress conforms to the shape of the body. This mattress is preferably placed on a manual or motorized bed frame that has the ability to be adjusted from a 0° to 90° upright position.

An object of the present invention is to provide an improved method of caring for ICU patients requiring up to 90° upright positions to reduce the risk of respiratory failure, refractory intracranial hypertension or increased abdominal pressures.

Another object of the present invention is to provide a mattress that will support a human body at rest whether in a 0° horizontal position or a 90° vertical upright position, supine or prone.

Another object of the present invention is to provide a mattress encased in a cover that will conform to a body's shape when a body's weight is placed upon the mattress and air is withdrawn from within the mattress cover causing a vacuum seal. This will allow the body to sink into the mattress, maintaining the body within the molded form of the mattress when in the upright or prone position.

Another object of the invention is to provide stability when the mattress is placed on a bed frame and transitioned into an upright position: up to 90° or greater, with the patient in either the supine or prone position.

The invention provides an improved method of caring for patients in the ICU with the option of mobilizing a patient in a position from a 0° to 90° upright, either supine or prone, position. These and other objects and advantages of the invention will become more apparent to a person of ordinary skill in the art in light of the following detailed description and appended drawings.

To the accomplishment of the above and related objects, this invention may be embodied in the form illustrated in the accompanying drawings, attention being called to the fact, however, that the drawings are illustrative only, and that changes may be made in the specific construction illustrated.

DETAILED DESCRIPTION OF THE INVENTION

Figure 1:
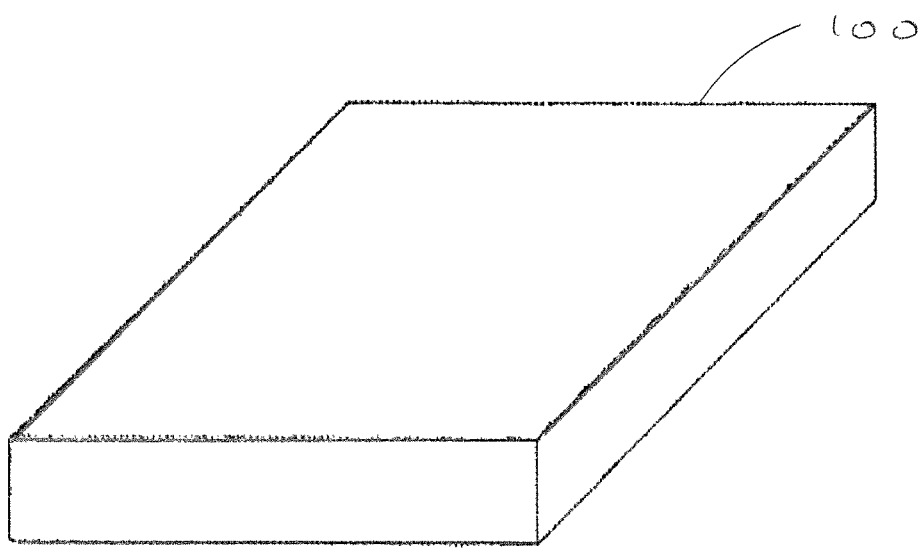
FIG. 1 is an illustration of a perspective view of the mattress according to a preferred embodiment.

Turning now descriptively to the drawings, in which similar reference characters denote similar elements throughout the several views, the attached figures illustrate a body positioning mattress, which comprises a mattress within a sealed, protective layer, a vacuum port and a final covering layer. The above mentioned mattress may be supported by a bed frame of choosing.

Figure 2:
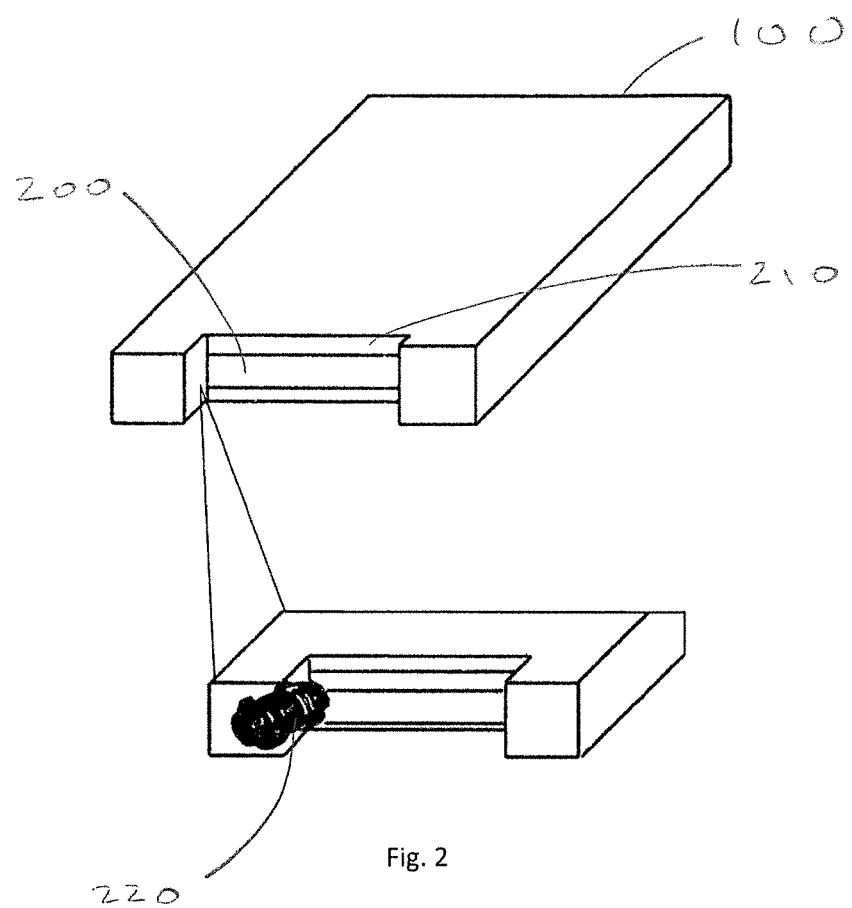
FIG. 2 is an illustration of a partial longitudinal cross-sectional perspective view of the mattress encased in a protective layer and showing a one-way valve used to remove air.
Figure 3:
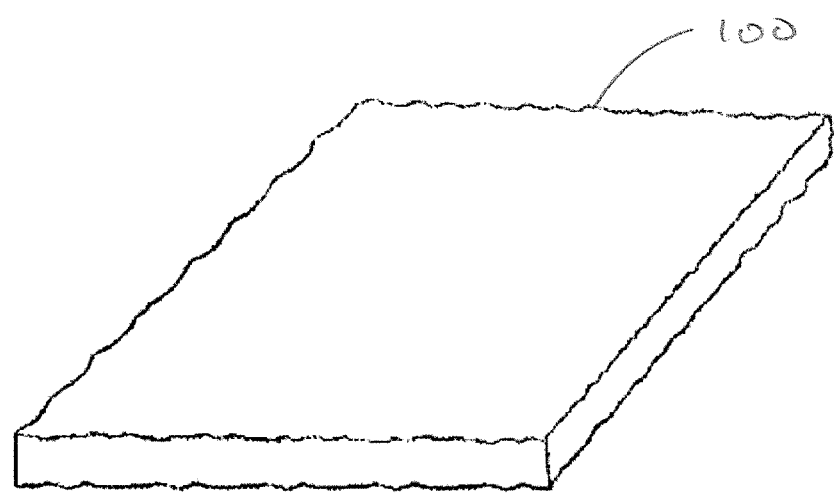
FIG. 3 is an illustration of a perspective view of the mattress that has been compressed after the air has been removed.

FIG. 1 shows the body positioning mattress (100) of the present invention. The body positioning mattress (100) includes a mattress (200) encased in an airtight cover (210) equipped with a suction valve (220). Preferably, a one-way valve is sealed within the mattress cover (210). When a vacuum process is applied through the valve (220), the mattress (200) will compress within the mattress cover (210) drawing the body of a patient (400) down into the mattress (200). The vacuum process may be applied by a hand held vacuum. FIG. 2 shows the body positioning mattress (100) with a mattress (200) inside of a sealed, protective layer (210) that has a vacuum port (220) used to remove air. FIG. 3 shows the body positioning mattress (100) of the present invention that has been compressed after the air has been removed from the mattress (200).

Figure 4A:
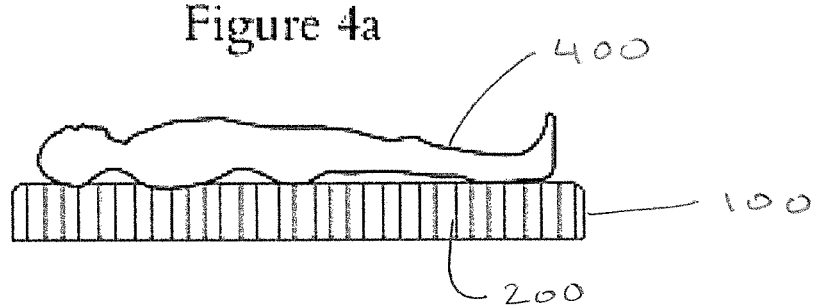
FIG. 4a is an illustration of a side plain view of a human body resting on the mattress before vacuum has been applied and air is removed.
Figure 4B:
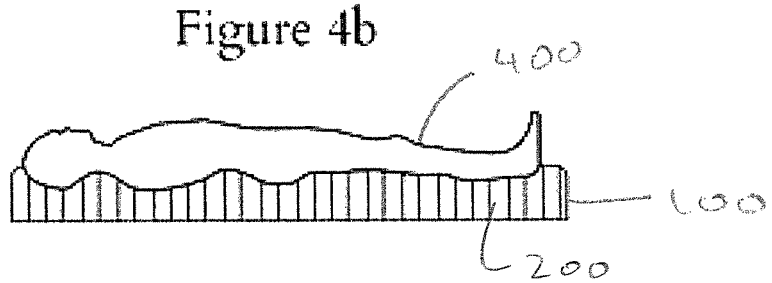
FIG. 4b is an illustration of a side plain view of a human body sinking into the mattress after vacuum has been applied and air is removed.

FIGS. 4a and 4b illustrate the patient (400) upon the body positioning mattress (100) before and after the vacuum process is applied to the mattress (200), such that the human body (400) sinks into the confines of the (200). This view is at 0° and does not reflect the utilization of a specially designed bed frame (500).

Figure 5A:
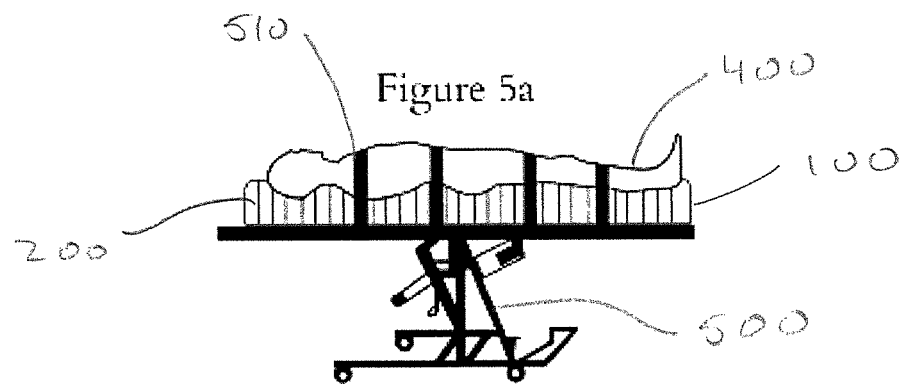
FIG. 5a is an illustration of a side plain view of a human body resting on the compressed mattress after suction has been applied, the mattress being on a specialty bed frame that utilizes safety straps to further secure the human body within the mattress to prevent slippage.
Figure 5B:
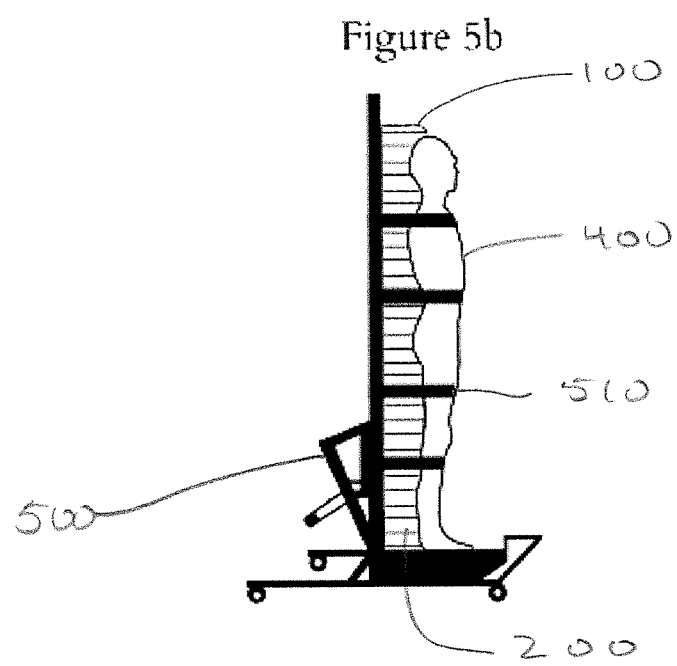
FIG. 5b is an illustration of a side plain view of a human body resting on the compressed mattress after suction has been applied, the mattress being on a specialty bed frame elevated to a 90° angle and that utilizes safety straps to further secure the human body within the mattress to prevent slippage.

FIGS. 5a and 5b show the body positioning mattress (100) with suction applied to the mattress (200) and placed on a specially designed bed frame (500). Safety straps (510) are utilized to further secure the human body (400) within the mattress (200) to prevent slippage and harm. FIG. 5b shows the patient (400) on the mattress (200) that has been placed on a specially designed bed frame (500) that may be positioned in the 90° upright position. Safety straps (510) are shown which are placed around the patient's body (400) to secure the body (400) to the mattress (200) and frame (500) preventing slippage and harm.

What we claim is:

1. A method of reducing the risk of respiratory failure in an immobile patient comprising the steps of:
   a) placing a body of the immobile patient on a mattress encased within an airtight cover;
   b) increasing a density of the mattress by removing air from the mattress to provide contour support of the body of the patient on the mattress by molding the mattress around the body;
   c) positioning the mattress in a standing upright position of about 90 degrees without any part of the body losing contact with the mattress; and
   d) maintaining the mattress in the standing upright position while maintaining a neutral skeletal alignment of the body; until the risk of hemodynamic instability, refractory intracranial hypertension or increased abdominal pressure of the bedridden patient is sufficiently reduced.

2. The method of claim 1, wherein the step of placing the body on the mattress comprises placing the body in one of a supine or prone position.

3. The method of claim 1, wherein the step of increasing the density of the mattress comprises removing air from the mattress with a vacuum process.

4. The method of claim 1, wherein the step of positioning the mattress comprises elevating the mattress with a bed frame selected from the group consisting of a manual bed frame and a motorized bed frame.

5. The method of claim 1, further comprising the step of further securing the body to the mattress with straps.

6. The method of claim 1, wherein the immobile patient is a ventilated patient.

* * * * *